(12) United States Patent
Lim et al.

(10) Patent No.: US 10,048,055 B2
(45) Date of Patent: Aug. 14, 2018

(54) OPTICAL PROBE AND OPTICAL COHERENCE TOMOGRAPHY APPARATUS INCLUDING THE SAME

(71) Applicants: Samsung Electronics Co., Ltd., Suwon-si (KR); Korea University Research and Business Foundation, Seoul (KR)

(72) Inventors: Jae-guyn Lim, Seongnam-si (KR); Hyun Choi, Seoul (KR); Min-seog Choi, Seoul (KR); Won-he Choe, Seoul (KR); Seong-deok Lee, Seongnam-si (KR); Woo-young Jang, Seongnam-si (KR); Beop-min Kim, Seoul (KR); Hyun-woo Jeong, Seoul (KR)

(73) Assignees: Samsung Electronics Co., Ltd., Suwon-si (KR); Korea University Research and Business Foundation, Seoul (KR)

( * ) Notice: Subject to any disclaimer, the term of this patent is extended or adjusted under 35 U.S.C. 154(b) by 319 days.

(21) Appl. No.: 13/737,370

(22) Filed: Jan. 9, 2013

(65) Prior Publication Data
US 2013/0176572 A1    Jul. 11, 2013

(30) Foreign Application Priority Data

Jan. 9, 2012   (KR) .................. 10-2012-0002469
Jul. 27, 2012  (KR) .................. 10-2012-0082564

(51) Int. Cl.
*G01B 9/02*   (2006.01)
*G02B 26/06*  (2006.01)
(Continued)

(52) U.S. Cl.
CPC ............. *G01B 9/02* (2013.01); *G01B 9/0201* (2013.01); *G01B 9/02058* (2013.01);
(Continued)

(58) Field of Classification Search
CPC ...................................................... G01B 9/02
(Continued)

(56) References Cited

U.S. PATENT DOCUMENTS

| 3,871,750 A | 3/1975 | Mecklenborg |
| 6,790,175 B1 | 9/2004 | Furusawa et al. |

(Continued)

FOREIGN PATENT DOCUMENTS

| CA | 2 555 477 A1 | 4/2007 |
| JP | 2007-209536 A | 8/2007 |

(Continued)

OTHER PUBLICATIONS

Extended European Search report dated Apr. 29, 2013, in counterpart European Patent Application No. 13150636.2 (6 pages in English).

(Continued)

*Primary Examiner* — Tarifur Chowdhury
*Assistant Examiner* — Omar Nixon
(74) *Attorney, Agent, or Firm* — NSIP Law

(57) ABSTRACT

An optical probe for irradiating light onto a subject includes an optical path control unit configured to receive light from outside the optical probe, and change a path of the light within the optical probe; an optical path length control element configured to receive the light having the changed path from the optical path control unit, and change an optical path length of the light as the optical path control unit changes the path of the light; and an optical output unit configured to receive the light having the changed optical path length from the optical path length control element, and output the light.

16 Claims, 9 Drawing Sheets

(51) Int. Cl.
 *G02B 26/10* (2006.01)
 *A61B 5/00* (2006.01)
(52) U.S. Cl.
 CPC ......... *G01B 9/02091* (2013.01); *G02B 26/06* (2013.01); *G02B 26/103* (2013.01); *G02B 26/105* (2013.01); *A61B 5/0066* (2013.01); *G01B 2290/65* (2013.01); *G02B 2207/117* (2013.01)
(58) Field of Classification Search
 USPC ........................................................ 356/479
 See application file for complete search history.

(56) References Cited

U.S. PATENT DOCUMENTS

| | | | |
|---|---|---|---|
| 7,557,931 B2* | 7/2009 | Toida | G01N 21/4795 356/497 |
| 8,274,721 B2 | 9/2012 | Cho et al. | |
| 8,831,700 B2 | 9/2014 | Schurman et al. | |
| 2003/0156323 A1* | 8/2003 | Overbeck | G02B 21/002 359/385 |
| 2005/0035295 A1* | 2/2005 | Bouma et al. | 250/341.1 |
| 2005/0168751 A1 | 8/2005 | Horii et al. | |
| 2006/0165350 A1 | 7/2006 | Gelikonov et al. | |
| 2006/0187462 A1* | 8/2006 | Srinivasan et al. | 356/479 |
| 2006/0232783 A1 | 10/2006 | Choma et al. | |
| 2007/0219437 A1 | 9/2007 | Schurman et al. | |
| 2008/0002183 A1 | 1/2008 | Yatagai et al. | |
| 2008/0170219 A1 | 7/2008 | Sarunic et al. | |
| 2010/0053636 A1 | 3/2010 | Holmes et al. | |
| 2010/0202030 A1 | 8/2010 | Cho et al. | |
| 2010/0321700 A1* | 12/2010 | Hirose | A61B 3/102 356/450 |
| 2011/0026035 A1* | 2/2011 | Muto | A61B 3/102 356/456 |
| 2011/0170111 A1 | 7/2011 | Rolland et al. | |
| 2011/0181889 A1* | 7/2011 | Kabetani | G01B 11/2441 356/496 |
| 2011/0279823 A1* | 11/2011 | Ueki | G01B 11/2441 356/511 |

FOREIGN PATENT DOCUMENTS

| | | |
|---|---|---|
| JP | 2009-529973 A | 8/2009 |
| JP | 2011-104266 A | 6/2011 |
| JP | 2011-117789 A | 6/2011 |
| KR | 10-2010-0075366 A | 7/2010 |
| KR | 10-2010-0090924 A1 | 8/2010 |
| KR | 10-2011-0041175 A | 4/2011 |
| WO | WO 2010/041182 A1 | 4/2010 |

OTHER PUBLICATIONS

B. Baumann et al., "Full range complex spectral domain optical coherence tomography without additional phase shifters," *Optics Express*, vol. 15, No. 20, Oct. 1, 2007, pp. 13375-13387 (article first published on Sep. 28, 2007).

Korean Office Action dated Apr. 19, 2018 in counterpart Korean Patent Application No. 10-2012-0082564 (17 pages, in Chinese with English translation).

* cited by examiner

OPTICAL PROBE AND OPTICAL COHERENCE TOMOGRAPHY APPARATUS INCLUDING THE SAME

CROSS-REFERENCE TO RELATED APPLICATIONS

This application claims the benefit of Korean Patent Application No. 10-2012-0002469 filed on Jan. 9, 2012, and Korean Patent Application No. 10-2012-0082564 filed on Jul. 27, 2012 in the Korean Intellectual Property Office, the disclosures of which are incorporated herein by reference in their entirety for all purposes.

BACKGROUND

1. Field

This application relates to an optical probe having a controllable optical path length and an optical coherence tomography (OCT) apparatus including the optical probe.

2. Description of Related Art

Recently, methods and apparatuses that are able to observe internal structures of subjects such as human tissues or various materials have been widely used. Examples of the apparatuses include an internal transmission image generating apparatus and a tomographic image generating apparatus such as an X-ray system, a computerized tomography (CT) scanner, a magnetic resonance image (MRI) apparatus, and an ultrasound system. These apparatuses may determine causes, locations, and progress of various diseases without having to directly incise internal structures of human or animal bodies, and accordingly hold a key position in the medical field. In these diagnosis apparatuses, safety in relation to human or animal bodies, acquisition of high resolution images, reasonable cost, and convenience of movement and use are important factors.

In particular, an optical coherence tomography (OCT) apparatus is an apparatus capable of capturing an internal structure of a subject based on interference between light irradiated on the subject and then reflected therefrom, and a reference light. The OCT apparatus has been widely used because it is capable of obtaining high resolution images and is harmless to human bodies.

SUMMARY

In one general aspect, an optical probe for irradiating light onto a subject includes an optical path control unit configured to receive light from outside the optical probe, and change a path of the light within the optical probe; an optical path length control element configured to receive the light having the changed path from the optical path control unit, and change an optical path length of the light as the optical path control unit changes the path of the light; and an optical output unit configured to receive the light having the changed optical path length from the optical path length control element, and output the light.

The optical output unit may be further configured to irradiate the light output from the optical output unit onto a subject; the optical path control unit may be further configured to change the path of the light to repeatedly move a point where the light output from the optical output unit is irradiated onto the subject by a predetermined distance in a predetermined direction; and the optical path length control element may be further configured to uniformly change the optical path length each time the point where the light is irradiated onto the subject moves.

The optical path length control element may be further configured to transmit the light having the changed path through the optical path length control element, and change the optical path length of the light according to a point of the optical path length control element through which the light passes.

The optical path length control element may have a nonuniform thickness, and may include a material having a uniform refractive index.

A cross-section of the optical path length control element may have a wedge shape.

At least one surface of the optical path length control element may have a meniscus shape.

The optical path length control element may include at least two materials having different refractive indexes.

The optical path length control element may include protrusions on a surface of the optical path length control element.

The optical path length control element may be further configured to change the optical path length of the light having the changed path by changing a diameter of the light having the changed path by blocking a portion of the light having the changed path.

The optical path length control element may be further configured to change the optical path length of the light have the changed path by changing the diameter of the light having the changed path according to the changed path.

The optical path control unit may include a mirror configured to rotate by a predetermined degree of rotation about a fixed axis of rotation each time the optical path control unit changes the path of the light.

In another general aspect, an optical coherence tomography (OCT) apparatus for scanning a subject by irradiating light onto the subject includes a light generator configured to generate light; a light coupler configured to split the generated light into a measurement light and a reference light, transmit the measurement light to an optical probe, and receive a response light from the optical probe, the response light being produced by the measurement light reflecting from the subject; a detector configured to detect an interference signal generated by interference between the response signal and the reference signal; and an image signal processor configured to generate a tomographic image of the subject from the detected interference signal; wherein the optical probe includes an optical path control unit configured to receive the measurement light from the light coupler, and change a path of the measurement light within the optical probe; an optical path length control element configured to receive the measurement light having the changed path from the optical path control unit, and change an optical path length of the measurement light as the optical path control unit changes the path of the measurement light; and an optical output unit configured to receive the measurement light having the changed optical path length from the optical path length control element, and output the measurement light.

The optical output unit may be further configured to irradiate the measurement light output from the optical output unit onto the subject; the optical path control unit may be further configured to change the path of the measurement light to repeatedly move a point where the measurement light output from the optical output unit is irradiated onto the subject by a predetermined distance in a predetermined direction; and the optical path length control element may be further configured to uniformly change the optical path length each time the point where the measurement light is irradiated onto the subject moves.

The optical path length control element may be further configured to transmit the measurement light having the changed path through the optical path length control element, and change the optical path length of the measurement light according to a point of the optical path length control element through which the measurement light passes.

The optical path length control element may have a nonuniform thickness, and may include a material having a uniform refractive index.

A cross-section of the optical path length control element may have a wedge shape.

At least one surface of the optical path length control element may have a meniscus shape.

The optical path length control element may include at least two materials having different refractive indexes.

The optical path length control element may include protrusions on a surface of the optical path length control element.

The optical path length control element may be further configured to change the optical path length of the measurement light having the changed path by changing a diameter of the measurement light having the changed patch by blocking a portion of the measurement light having the changed path.

The optical path length control element may be further configured to change the optical path length of the measurement light having the changed path by changing the diameter of the measurement light having the changed patch according to the changed path.

The optical path control unit may include a mirror configured to rotate by a predetermined degree of rotation about a fixed axis of rotation each time the optical path control unit changes the path of the measurement light.

In another general aspect, an optical probe includes an optical path control unit configured to receive light, and control a path of the light; and an optical path length modulator having no moving parts and being configured to receive the light having the controlled path from the optical path control unit, and modulate an optical path length of the light having the controlled path as the optical path control unit controls the path of the light.

The optical path length modulator may be a passive optical path length modulator configured to modulate the optical path length of the light having the controlled path without any external control as the optical path control unit controls the path of the light.

The optical path length modulator may be further configured to modulate the optical path length of the light having the controlled path according to a characteristic of the optical path length modulator depending on a point where the light having the controlled path is incident on the optical path length modulator.

The characteristic of the optical path length modulator may be an optical path length of the optical path length modulator.

Other features and aspects will be apparent from the following detailed description, the drawings, and the claims.

DETAILED DESCRIPTION

Figure 1:
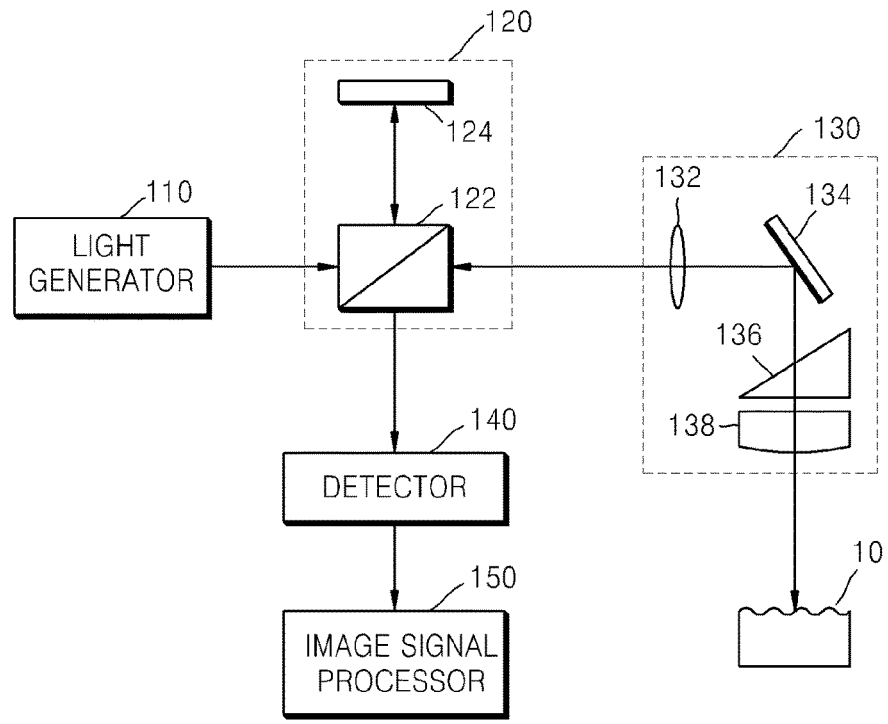
FIG. 1 illustrates a configuration of an example of an optical coherence tomography (OCT) apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 illustrates a configuration of an example of an optical coherence tomography (OCT) apparatus. Referring to FIG. 1, the OCT apparatus includes a light generator 110, a light coupler 120, an optical probe 130, a detector 140, and an image signal processor 150. The operation of the OCT apparatus will be described with reference to FIG. 1 below.

The light generator 110 generates light and transmits the light to the light coupler 120. The light coupler 120 includes a beam splitter 122 and a reference mirror 124. The light transmitted from the light generator 110 is split into a measurement light and a reference light in the beam splitter 122. The measurement light is transmitted to the optical probe 130, and the reference light is transmitted to the reference mirror 124 and reflected from the reference mirror 124. The reflected reference light returns to the beam splitter 122. The measurement light transmitted to the optical probe 130 is irradiated onto a subject 10 of which an internal tomographic image is to be captured through the optical probe 130. A response light generated by the irradiated measurement light reflecting from the subject 10 is transmitted to the beam splitter 122 of the light coupler 120 through the optical probe 130. The transmitted response light and the reference light reflected from the reference mirror 124 interfere with each other in the beam splitter 122, and the detector 140 detects an interference signal. The detector 140 transmits the detected interference signal to the image signal processor 150, and the image signal processor 150 converts the detected interference signal into an image signal representing a tomographic image of the subject 10.

Since this example relates to a full range OCT apparatus, the full range OCT apparatus and an internal configuration and an operation of the optical probe 130 used for implementing the full range OCT apparatus will be described below.

The full range OCT apparatus changes an optical path length of a measurement light as a point of the subject 10 onto which the measurement light is irradiated moves in a lateral direction, thereby modulating the optical path length of the measurement light as the point of the subject 10 onto which the measurement light is irradiated moves in the lateral direction. This optical path length modulation modulates the phase of the interference signal detected by the detector 140. In greater detail, a scan is performed by continuously moving a point of the subject 10 onto which the measurement light is irradiated by the same distance in a lateral direction. In addition, optical path length modulation, and thus phase modulation of the interference signal detected by the detector 140, is performed by increasing the optical path length of the measurement light by the same length whenever the point of the subject 10 onto which the measurement light is irradiated moves in the lateral direction. A direction in which the measurement light is irradiated onto the subject 10, that is, a depth direction of the subject 10, is referred to as an axial direction, and a direction perpendicular to the axial direction is referred to as a lateral direction.

The optical path length is a value obtained by multiplying a refractive index n of a medium through which the measurement light travels by a distance l the measurement light travels through the medium having the refractive index n. That is, the optical path length is equal to a distance the measurement light would travel through a vacuum during the time it takes for the measurement light to travel through the medium having the refractive index n.

Accordingly, as described above, the optical probe 130 moves a point of the subject 10 onto which the measurement light is irradiated in the lateral direction while changing the optical path length of the measurement light.

Referring to FIG. 1, the optical probe 130 includes a collimator lens 132, a galvano scanner 134, an optical path length control element 136, and a lens 138. The galvano scanner 134 is a mirror that can be rotated by a predetermined degree of rotation about a predetermined axis of rotation, and may be a microelectromechanical system (MEMS) scanner that obtains a driving power necessary for rotation from a MEMS. The optical path length control element 136 may be formed in various shapes of a single material having a uniform refractive index, or two or more materials having different refractive indexes, and controls the optical path length to be changed according to a point of the optical path length control element 136 through which the measurement light passes.

The measurement light transmitted from the beam splitter 122 is collimated by passing through the collimator lens 132 of the optical probe 130. The measurement light that has passed through the collimator lens 132 is reflected from the galvano scanner 134 in a particular direction determined by a rotary position of the galvano scanner 134 about an axis of rotation of the galvano scanner 134, and then the reflected measurement light sequentially passes through the optical path length control element 136 and the lens 138, and is irradiated onto the subject 10. As the galvano scanner 134 rotates about the predetermined axis of rotation, the point of the subject 10 onto which the measurement light is irradiated moves in the lateral direction, thereby changing the direction of the measurement light, and also a point of the optical path length control element 136 through which the measurement light passes moves, thereby changing the optical path length of the measurement light.

Although not illustrated in FIG. 1, the optical probe 130 may include a housing (not shown) that contains the collimator lens 132, the galvano scanner 134, the optical path length control element 136, and the lens 138. In this case, the measurement light that has passed through the optical path length control element 136 and the lens 138 is output from an opening of the housing and is then irradiated onto the subject 10. Thus, the opening of the housing may be referred to as a light opening.

A method of scanning the measurement light in the lateral direction on the subject 10 while changing the optical path length will now be explained with reference to FIG. 2.

Figure 2:
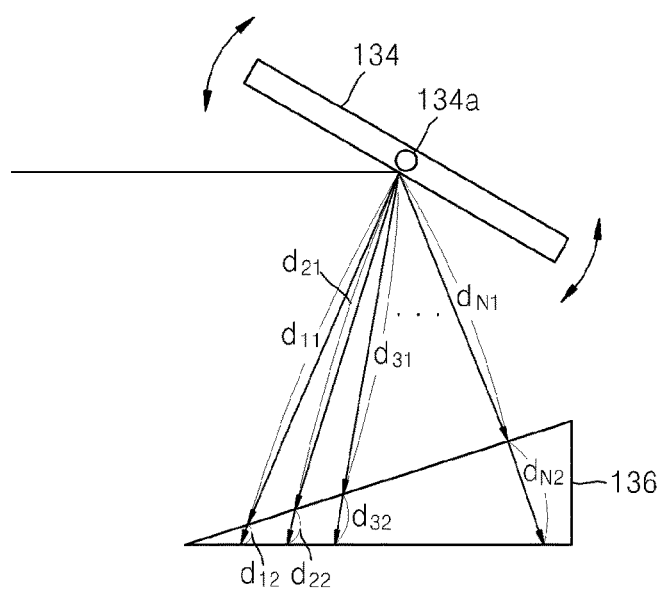
FIG. 2 illustrates an example of a path through which measurement light travels in an optical probe.

FIG. 2 illustrates an example of a path through which the measurement light travels in the optical probe 130. Referring to FIG. 2, a direction of the measurement light is moved by a predetermined distance in the lateral direction as the galvano scanner 134 rotates by a predetermined degree of rotation about an axis of rotation 134a. The galvano scanner 134 rotates to change the direction of the measurement light from a first direction to an N-th direction. A measurement light of the first direction travels through an optical path length corresponding to $d_{11}$ and $d_{12}$ in FIG. 2, a measurement light of the second direction travels through an optical path length corresponding to $d_{21}$ and $d_{22}$ in FIG. 2, and a measurement light of the N-th direction travels through an optical path length corresponding to $d_{N1}$ and $d_{N2}$ in FIG. 2. If it is assumed that $d_i$ is an optical path length through which the measurement light travels after being reflected from the galvano scanner 134 until it passes through the optical path length control element 136, $d_i$ may be expressed by the following Equation 1.

$$d_i = d_{i1} + n \times d_{i2} \quad (1)$$

In Equation 1, n denotes a refractive index of a material of the optical path length control element 136.

A difference between optical path lengths of two measurement lights of adjacent directions, that is, a difference between an optical path length of a measurement light of an (i+1)-th direction and an optical path length of a measurement light of an i-th direction, may be expressed by the following Equation 2.

$$\Delta x = d_{i+1} - d_i \quad (2)$$

Thus, $\Delta x$ is the amount the optical path length of the measurement light changes, i.e., the amount by the optical path length is modulated, each time the galvano scanner 134 moves the direction of the measurement light by the predetermined distance in the lateral direction. Accordingly, $\Delta x$ may be considered to be a modulation index of the optical path length modulation. The modulation index $\Delta x$ may be changed by adjusting an angle between an inclined plane of the optical path length control element 136 and a base plane thereof, the refractive index of the material of the optical path length control element 136, a position of the axis of rotation 134a of the galvano scanner 134, or a curvature of the reflective surface of the galvano scanner 134. A detailed method of performing the optical path length modulation using the modulation index $\Delta x$ will be explained in detail below.

If $\Delta x$ of Equation 2 is $$\frac{1}{f_B},$$

a power of an interference signal that is received from the detector 140 of the OCT apparatus of FIG. 1 is represented by the following Equation 3.

$$I_D(k_i, x) = S(k_i)\sum_{n=1}^{N}\rho_n(x)\cos(2k_i\Delta z + f_B x) + DC \quad (3)$$

In Equation 3, x denotes a coordinate of a point of the subject 10 onto which the measurement light is irradiated, assuming that the lateral direction in which a direction of the measurement light moves is an X axis, $k_i$ denotes a wavenumber of the measurement light of the i-th direction, $I_D$ denotes the power of the interference signal that is received from the detector 140, $S(k_i)$ denotes an amplitude of each wavenumber of a light source, $\rho_n(x)$ denotes an amplitude of the light source in the lateral direction, $\Delta z$ denotes a difference value obtained by subtracting a distance that light travels from the beam splitter 122 to the reference mirror from a distance that light travels from the beam splitter 122 to the subject 10, and DC denotes a DC component.

The following Equation 4 is obtained by rewriting Equation 3 with terms including a complex number in exponential form using Euler's formula.

$$I_D(k_i,x) = A(k_i)e^{2if_Bx} + A^*(k_i,x)e^{-2if_Bx} + DC \quad (4)$$

In order to perform the optical path length modulation, as described above, an optical path length is increased by a constant value when a direction of the measurement light is changed as expressed by the following Equation 5.

$$d_{(i+2)} - d_{(i+1)} = d(i+1-d_i) \quad (5)$$

For example, an increase in the optical path length when the direction of the measurement light is changed from the first direction to the second direction is the same as an increase in the optical path length when the direction of the measurement light is changed from the second direction to a third direction.

Also, as described above, the modulation index of the optical path length modulation may be changed by adjusting an angle between the inclined plane of the optical path length control element 136 and the base plane thereof, the refractive index of the material of the optical path length control element 136, the position of the axis of rotation 134a of the galvano scanner 134, or a curvature of the reflective surface of the galvano scanner 134.

Conventional coherence tomography apparatuses do not include a an element corresponding to the optical path length control element 136, but use a method of moving the axis of rotation of a galvano scanner to make constant a difference $\Delta x$ between optical path lengths of two measurement lights of adjacent directions in performing optical path length modulation.

Thus, the conventional coherence tomography apparatuses have a limit in terms of miniaturization thereof since a space for moving the axis of rotation of the galvano scanner is required. For example, when a MEMS scanner having a total width of 3 mm and a mirror having a diameter of 1.5 mm is used as the galvano scanner in an optical probe of a conventional coherence tomography apparatus, an additional width of 500 μm through 700 μm is required for moving the axis of rotation of the galvano scanner, requiring a total width of 3.5 mm to 3.7 mm. Accordingly, such an optical probe cannot be inserted into a working channel of an endoscope having a standard diameter of 2.8 mm to 3.0 mm. However, in the example described herein, optical path length modulation may be performed without moving the axis of rotation of the galvano scanner 134 by including the optical path length control element 136, and accordingly a full range OCT apparatus may be implemented without increasing the width of the optical probe 130.

Various examples of the optical path length control element 136 and the optical probe 130 including the optical path length control element 136 will described below with reference to FIGS. 3A through 3C.

Figure 3A:
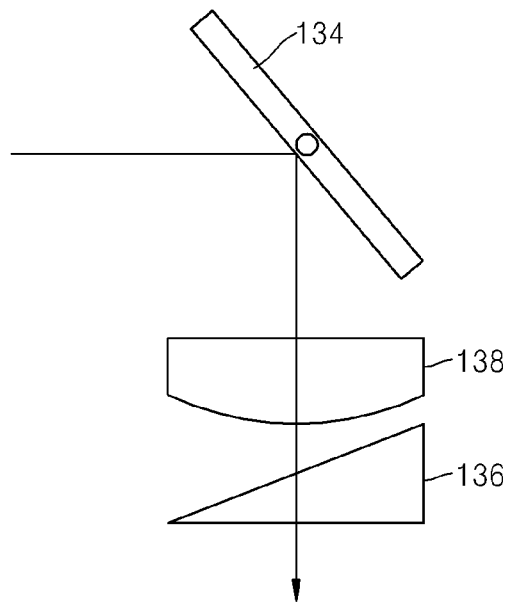
FIGS. 3A through 3C illustrate internal configurations of examples of optical probes including an optical path length control element.
Figure 3B:
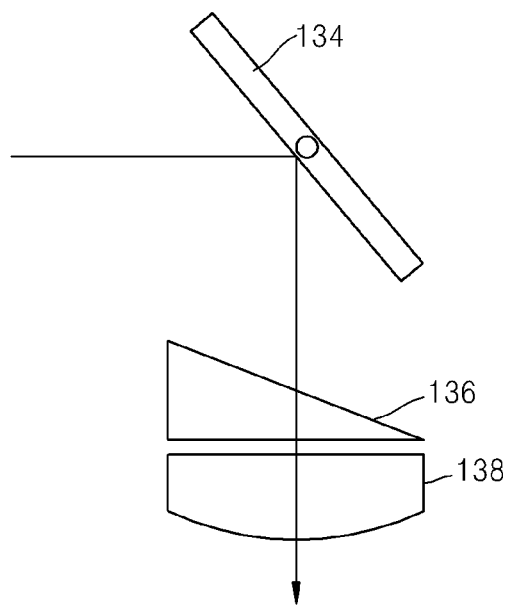
Figure 3C:
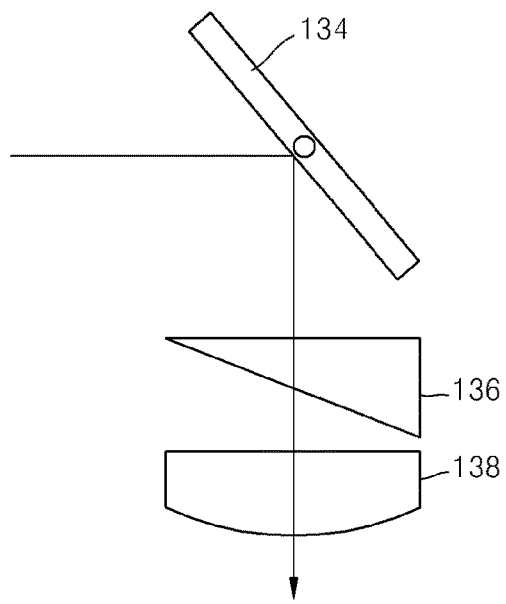

FIGS. 3A through 3C illustrate internal configurations of examples of optical probes including the optical path length control element 136. In greater detail, FIGS. 3A through 3C illustrate examples of optical probes in which locations and orientations of the optical path length control element 136 differ in each example from the example illustrated in FIGS. 1 and 2.

Referring to FIG. 3A, the optical path length control element 136 is disposed below the lens 138, compared to being disposed above the lens 138 in the example illustrated in FIGS. 1 and 2, but is oriented the same as in the example illustrated in FIGS. 1 and 2.

Referring to FIG. 3B, the location where the optical path length control element 136 is disposed is the same as in the example illustrated in FIGS. 1 and 2, but the left and right sides of the optical path length control element 136 are reversed compared to the example illustrated in FIGS. 1 and 2, i.e., the optical path length control element 136 is flipped in the horizontal direction in the example illustrated in FIG. 3B compared to the example illustrated in FIGS. 1 and 2.

Referring to FIG. 3C, the location where the optical path length control element 136 is disposed is the same as in the example illustrated in FIGS. 1 and 2, but the upper and lower sides of the optical path length control element 136 are reversed compared to the example, illustrated in FIGS. 1 and 2, i.e., the optical path length control element 136 is flipped in the vertical direction in the example illustrated in FIG. 3C compared to the example illustrated in FIGS. 1 and 2.

Accordingly, as described above, the location and the orientation of the optical path length control element 136 in the optical probe may be changed in various ways if necessary. The modulation index of the optical path length modulation may be changed by adjusting an angle between the inclined plane of the optical path length control element 136 and the base plane thereof, the refractive index of the material of the optical path length control element 136, the position of the axis of rotation 134a of the galvano scanner 134, or a curvature of the reflective surface of the galvano scanner 134.

Figure 4A:
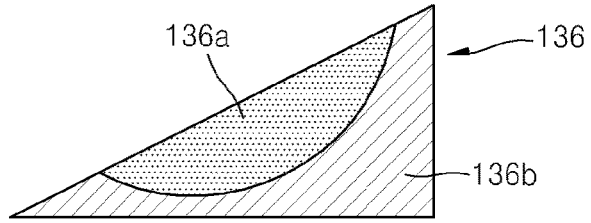
FIGS. 4A through 4C illustrate cross-sectional views of other examples of the optical path length control element.
Figure 4B:
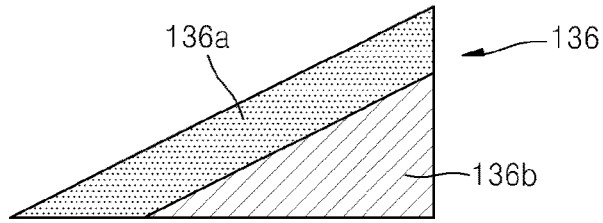
Figure 4C:
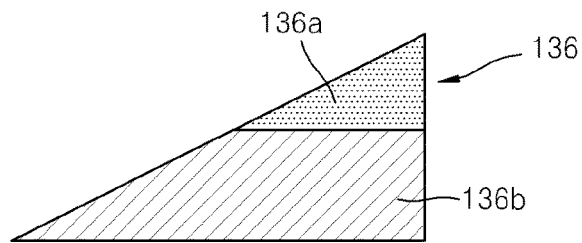

FIGS. 4A through 4C illustrate cross-sectional views of other examples of the optical path length control element 136. In greater detail, FIGS. 4A through 4C illustrate examples in which the optical path length control element 136 made of two different materials having different refractive indexes. In FIGS. 4A through 4C, reference numerals 136a and 136b indicate two different materials having different refractive indexes.

Referring to FIG. 4A, a boundary line between the material 136a and the material 136b is a curved line extending from the upper surface of the optical path length control element 136 into the interior of the optical path length control element 136 and back to the upper surface of the optical path length control element 136.

Referring to FIG. 4B, a boundary line between the material 136a and the material 136b is a straight line parallel to the upper surface of the optical path length control element 136.

Referring to FIG. 4C, a boundary line between the material 136a and the material 136b is a straight line parallel to the bottom surface of the optical path length control element 136.

Accordingly, as described above, a material that forms the optical path length control element 136 may be changed if necessary. The modulation index of the optical path length modulation may be changed by adjusting an angle between the inclined plane of the optical path length control element 136 and the base plane thereof, the refractive indexes of the materials of the optical path length control element 136, the position of the axis of rotation 134a of the galvano scanner 134, or a curvature of the reflective surface of the galvano scanner 134. In addition, although in FIGS. 4A through 4C the optical path length control element 136 is made of two different materials 136a and 136b having different refractive indexes, the optical path length control element 136 may be made of three or more different materials having different refractive indexes.

FIGS. 5A through 5E illustrate cross-sectional views of other examples of the optical path length control element 136 having different shapes. In FIGS. 1 through 4C, the cross-section of the optical path length control element 136 has a wedge shape. However, as shown in FIGS. 5A through 5E, the cross-section of the optical path length control element 136 may have different shapes.

Figure 5A:
FIGS. 5A through 5E illustrate cross-sectional views of other examples of the optical path length control element having different shapes.

Referring to FIG. 5A, the upper and lower surfaces of the optical path length control element 136 have a meniscus shape. Alternatively, although not illustrated in FIG. 5A, only one of the upper and lower surfaces of the optical path length control element 136 may have a meniscus shape.

Figure 5B:
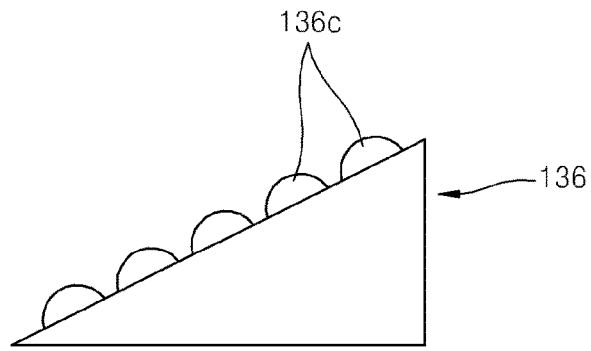

Referring to FIG. 5B, the upper surface of the optical path length control element 136 has protrusions 136c.

Figure 5C:
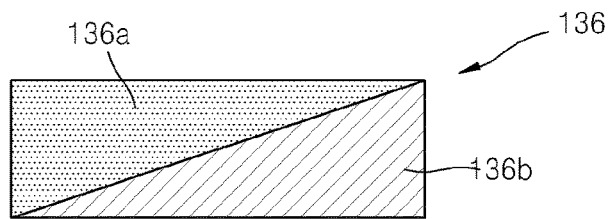

Referring to FIG. 5C, the cross-section of the optical path length control element 136 has a rectangular formed by two wedge-shaped layers 136a and 136b made of two different materials having different refractive indexes.

Figure 5D:
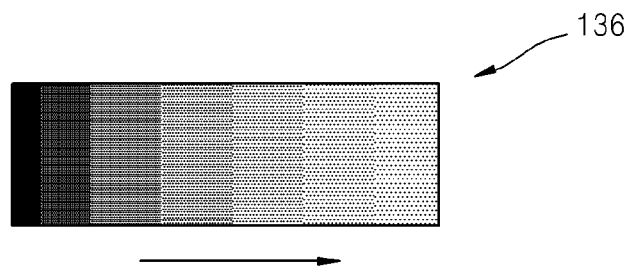

Referring to FIG. 5D, the cross-section of the optical path length control element 136 has a rectangular shape, and a refractive index of the optical path length control element 136 gradually changes in a direction parallel to the upper and lower surfaces of the optical path length control element 136 as indicated by the gradually increasing shades of gray indicating different refractive indexes. In FIG. 5D, the different shades of gray indicate different refractive indexes. The refractive index may change in discrete steps as illustrated in FIG. 5D, or may change continuously.

Figure 5E:
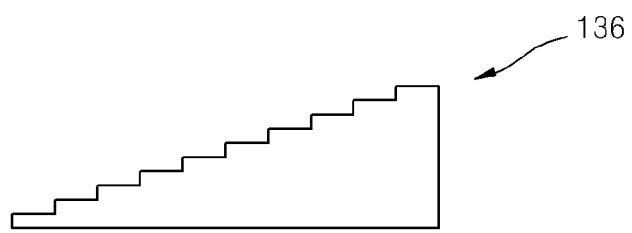

Referring to FIG. 5E, the cross-section of the optical path length control element 136 has a stair shape.

By using various shapes for the cross-section of the optical path length control element 136 as described above, non-linear characteristics that may be generated while performing optical path length modulation in an optical probe including the optical path length control element 136 may be corrected. In addition, a modulation degree of the optical path length modulation may be changed by adjusting an angle between the inclined plane of the optical path length control element 136 and the base plane thereof, the refractive index of the material of the optical path length control element 136, the position of the axis of rotation 134a of the galvano scanner 134, or a curvature of the reflective surface of the galvano scanner 134.

Figure 6:
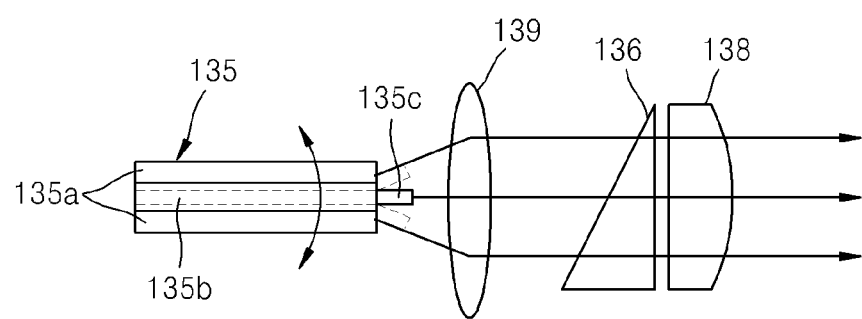
FIG. 6 illustrates an internal configuration of an example of an optical probe including a piezoelectric actuator.

FIG. 6 illustrates an internal configuration of an example of an optical probe including a piezoelectric actuator 135. The optical probe illustrated in FIG. 6 changes the direction of a measurement light using the piezoelectric actuator 135, rather than the galvano scanner 134 used in the optical probe 130 illustrated in FIG. 1. In greater detail, if an electrical signal is applied to piezoelectric elements 135a disposed in the upper portion and the lower portion of the piezoelectric actuator 135, the piezoelectric elements 135a are bent upward or downward, and a supporting layer 135b of the piezoelectric actuator 135 that supports the piezoelectric elements 135a is also bent upward or downward as the piezoelectric elements 135a are bent upward or downward. The supporting layer 135b includes an optical fiber 135c through which the measurement light is transmitted, and a direction of the measurement light that is output from the optical fiber 135c is changed upward or downward since the optical fiber 135c is bent upward or downward together with the supporting layer 135b. The measurement light of different directions that is output from the optical fiber 135c is collimated by a collimator lens 139, and then sequentially passes through an optical path length control element 136 and a lens 138, and is irradiated onto a subject (not illustrated in FIG. 6).

In the optical probe of FIG. 6, optical path length modulation by rotating a galvano scanner about its axis of rotation like the galvano scanner 134 in the optical probe 130 illustrated in FIG. 1 is impossible because such a galvano scanner is not used in the optical probe in FIG. 6. However, by disposing the optical path length control element 136 in a path of the measurement light of different directions that is output from the optical fiber 135c as illustrated in FIG. 6, the optical path length modulation described above may be performed. The optical path length control element 136 in FIG. 6 may have any of the various forms illustrated in FIGS. 4A through 5E. Accordingly, by using the piezoelectric actuator 135 and the optical path length control element 136, a full range OCT apparatus may be implemented using an optical probe in which moving the axis of rotation of a galvano scanner is impossible.

Optical path length modulation for performing phase modulation may also be performed by changing a diameter of measurement as will be described in greater detail below.

Figure 7A:
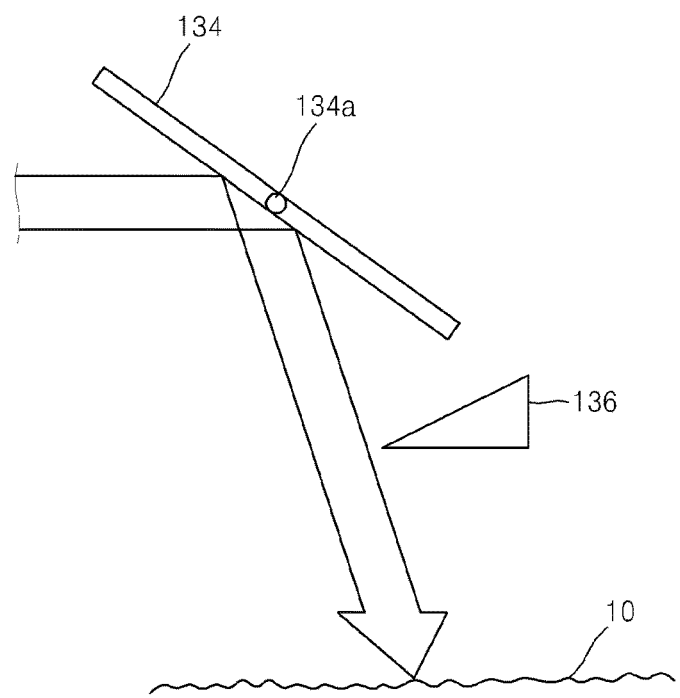
FIG. 7A illustrates an example of a path through which measurement light travels in an optical probe.
Figure 7B:
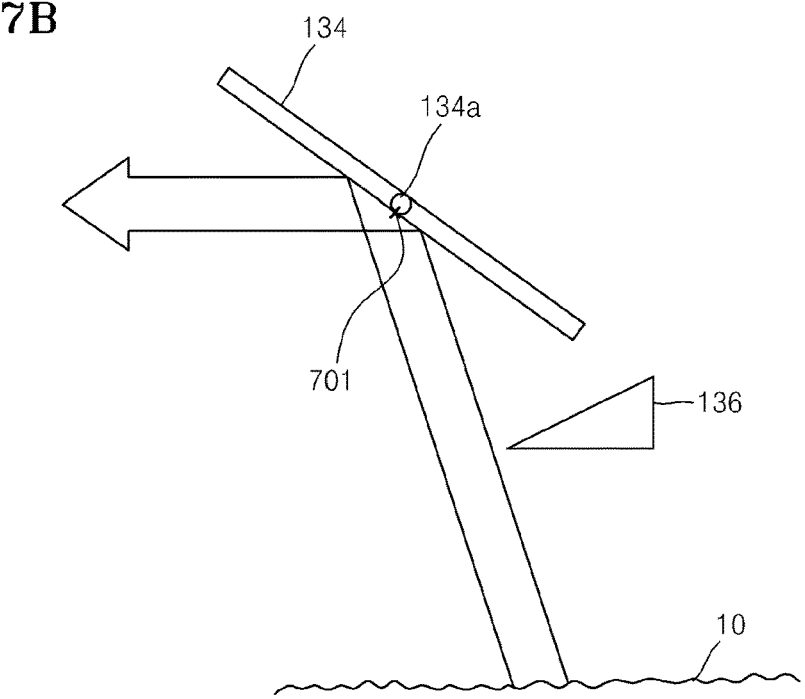
FIG. 7B illustrates an example of a path through which reflection light travels in an optical probe.

FIG. 7A illustrates an example of a path through which measurement light travels in an optical probe, and FIG. 7B illustrates an example of a path through which response light, i.e., reflection light, travels in an optical probe.

Referring to FIG. 7A, the measurement light is reflected from the galvano scanner 134 in a first direction determined by a first rotary position of the galvano scanner 134 about the axis of rotation 134a, and the measurement light of the first direction is irradiated onto the subject 10. In this case, the optical path length control element 136 is not located in a path of the measurement light. Accordingly, the measurement light is irradiated onto the subject 10 without being influenced by the optical path length control element 136.

Referring to FIG. 7B, reflection light produced by the measurement light reflecting from the subject 10 is reflected from the galvano scanner 134 without being influenced by the optical path length control element 136, and then travels to the outside of the optical probe.

Figure 8A:
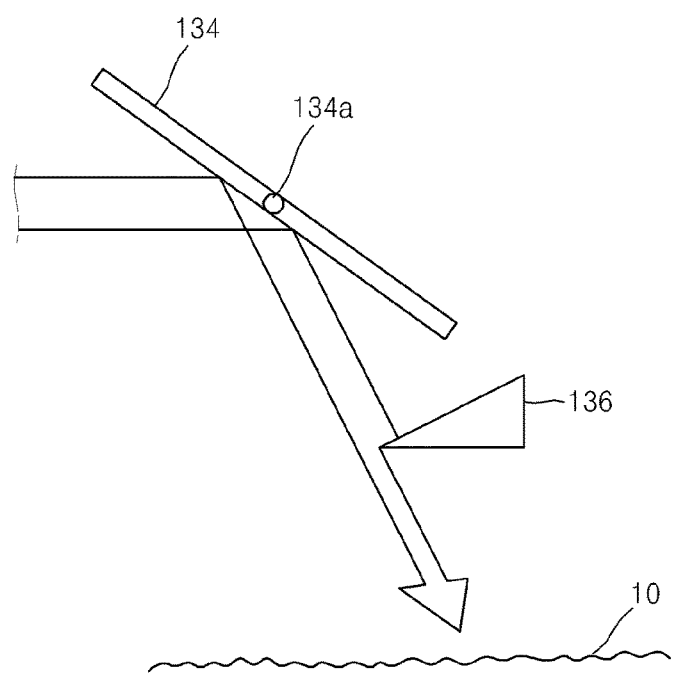
FIG. 8A illustrates another example of a path through which measurement light travels in an optical probe.
Figure 8B:
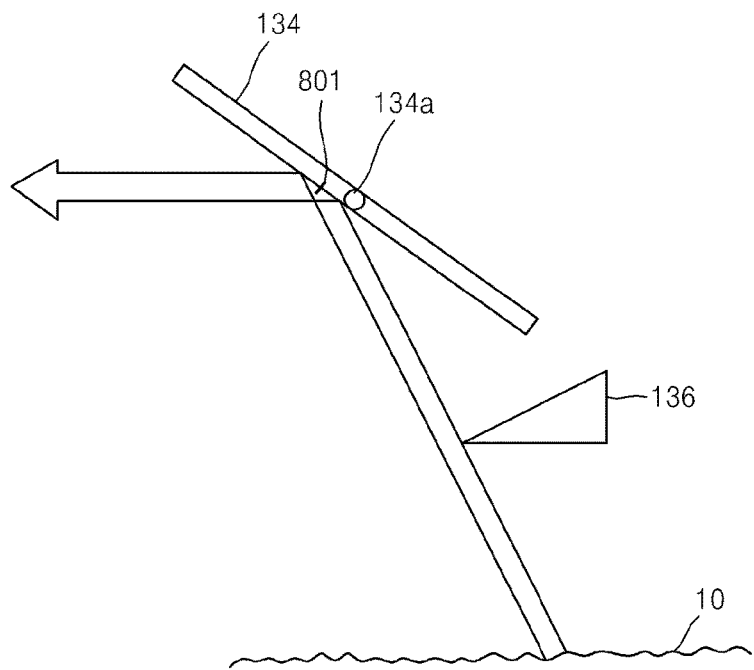
FIG. 8B illustrates another example of a path through which reflection light travels in an optical probe.

FIG. 8A illustrates another example of a path through which measurement light travels in an optical probe, and FIG. 8B illustrates another example of a path through which response light, i.e., reflection light, travels in an optical probe.

Referring to FIG. 8A, the galvano scanner 134 has rotated counterclockwise about the axis of rotation 134a compared to FIG. 7A to a second rotary position about the axis of rotation 134a, and accordingly a direction of the measurement light reflected by the galvano scanner 134 has moved to the right compared to the direction of the measurement light in FIG. 7A. The measurement light is reflected from the galvano scanner 134 in a second direction different from the first direction of the measurement light in FIG. 7A, and the measurement light of the second direction is irradiated onto the subject 10. In this case, the optical path length control element 136 is located in a path of the measurement light. Accordingly, a portion of the measurement light of the second direction is refracted or blocked by the optical path length control element 136, and thus deviates from the second direction, and only a remaining portion of the measurement light continues traveling in the second direction and is irradiated onto the subject 10. That is, the diameter of the measurement light that reaches the subject 10 is reduced compared to FIG. 7A. The optical path length control element 136 may be made in various shapes of one material having a constant refractive index or two or more materials having different refractive indexes. Alternatively, the optical path length control element 136 may be made of a material that blocks light.

Referring to FIG. 8B, reflection light produced by the measurement light reflecting from the subject 10 is reflected from the galvano scanner 134, and then travels to the outside of the optical probe. In this case, the diameter of the reflection light illustrated in FIG. 8B is also reduced compared to FIG. 7B due to the optical path length control element 136 refracting or blocking a portion of the measurement light in FIG. 8A.

Accordingly, as described above, the optical path length control element 136 changes the diameters of the measurement light and the reflection light, which substantially changes the length of an optical path. The reason that the changes in the diameters of the measurement light and the reflection light change the length of the optical path will now be described in detail with reference to FIGS. 7B and 8B.

Comparing a central point 701 of a diameter of the reflection light on the galvano scanner 134 in FIG. 7B with a central point 801 of a diameter of the reflection light on the galvano scanner 134 in FIG. 8B, the position of the central point 701 and the position of the central point 801 are different from each other. That is, as the diameter of the reflection light on the galvano scanner 134 changes, the position of the central point of the diameter of the reflection light on the galvano scanner 134 changes. Since a distance that light travels is substantially a distance that the central point of the diameter of the light travels, optical path lengths of the measurement light and the reflection light illustrated in FIG. 7B are different from the optical path lengths of the measurement light and the reflection light illustrated in FIG. 8B. Accordingly, optical path lengths of the measurement light and the reflection light may be changed by changing the diameters of the measurement light and the reflection light using the optical path length control element 136 as described above.

A specific method of performing optical path length modulation to perform phase modulation by changing the diameter of measurement light will now be described.

Figure 9:
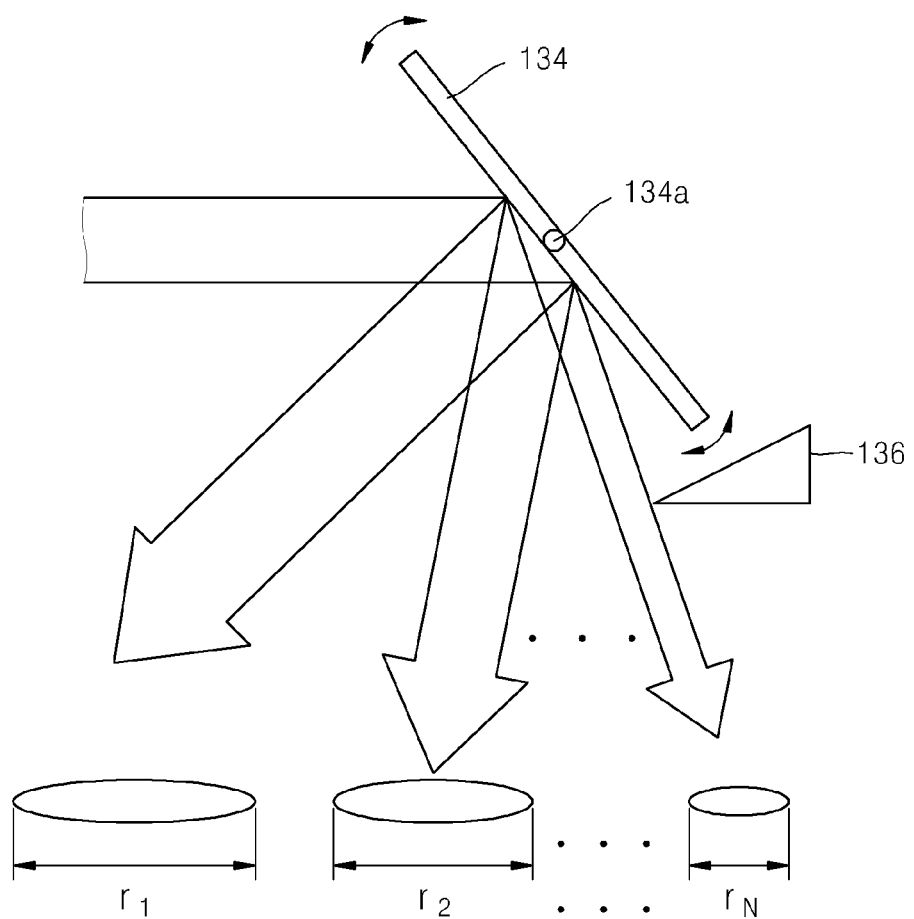
FIG. 9 illustrates another example of a path through which measurement light travels in an optical probe.

FIG. 9 illustrates another example of a path through which measurement light travels in an optical probe. Referring to FIG. 9, the diameter of measurement light of a first direction is $r_1$, the diameter of measurement light of a second direction is $r_2$, and the diameter of measurement light of an N-th direction is $r_N$. The diameters are changed using the optical path length control element 136 as described above with reference to FIGS. 7A through 8B. If the diameter of a measurement light of an i-th direction is $r_i$ (where i is 1, 2, ..., or N), a difference between diameters of two measurement lights of adjacent directions (that is, a measurement light of an i+1-th direction and a measurement light of an i-th direction) may be expressed by the following Equation 6.

$$\Delta r = r_{i+1} - r_i \quad (6)$$

If $\Delta r$ of Equation 6 is $$\frac{1}{f_B},$$

the optical path length modulation for performing phase modulation may be performed according to Equations 3 and 4 described above. Refer to the descriptions of Equations 3 and 4 above for more details.

Another optical probe may include a lens having a modified shape that simultaneously performs a function of a lens and a function of an optical path length control element. Examples of such an optical probe will be described in greater detail below with reference to FIGS. 10A and 10B.

Figure 10A:
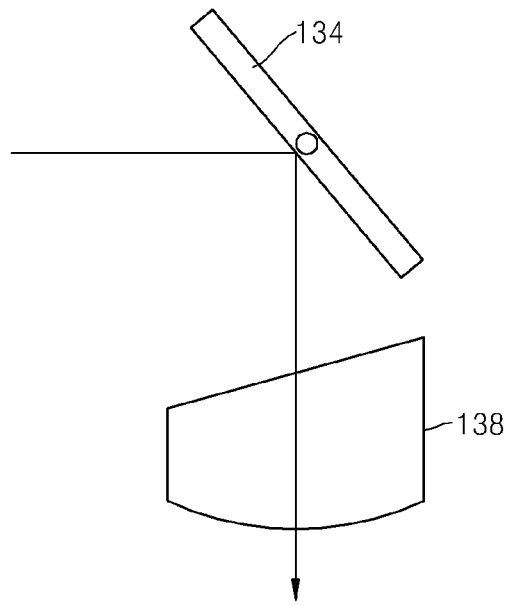
FIGS. 10A and 10B illustrate internal configurations of other examples of optical probes.
Figure 10B:
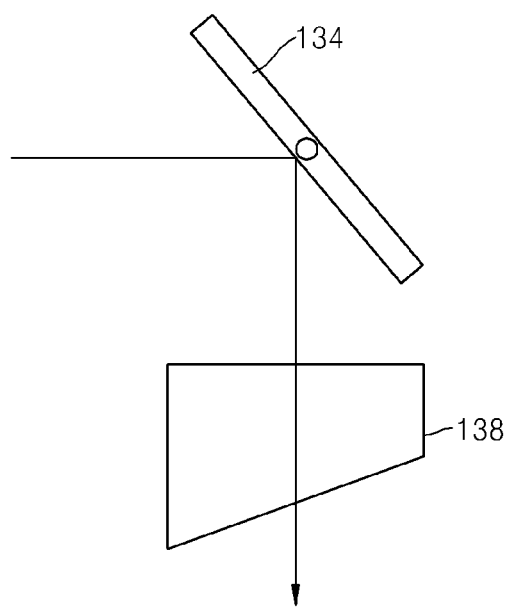

FIGS. 10A and 10B illustrate internal configurations of other examples of optical probes. Comparing FIGS. 10A and 10B with FIGS. 3A through 3C, the optical probes of FIGS. 3A through 3C include the optical path length control element 136 and the lens 138 as separate elements, whereas the optical probes of FIGS. 10A and 10B do not include the optical path length control element 136, but include only the lens 138. In this case, one surface of the lens 138 of FIGS. 10A and 10B is formed as an inclined plane like the inclined plane of the optical path length control element 136 of FIGS. 3A to 3C, and accordingly the shape of the lens 138 of FIGS. 10A and 10B is similar to a shape obtained by combining the optical path length control element 136 of FIGS. 3A to 3C with an upper or lower surface of the lens 138 of FIGS. 3A through 3C. That is, the lens 138 of FIGS. 10A and 10B simultaneously performs the functions of the optical path length control element 136 and the lens 138 of FIGS. 3A through 3C. The lens 138 of FIGS. 10A and 10B enables a configuration of an optical probe to be simplified by providing the function changing an optical path length by modifying a lens.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An optical probe for irradiating light onto a subject, the optical probe comprising:
an optical path control unit configured to receive light from outside the optical probe, and to change a path of the light within the optical probe by repeatedly moving a direction in which the light is irradiated onto the subject by a constant lateral distance;

an optical path length control element configured to receive the light having the changed path from the optical path control unit, and to increase an optical path length of the light having the changed path by a constant value each time the direction in which the light is irradiated onto the subject moves by the constant lateral distance by changing a diameter of the light having the changed path by blocking a portion of the light having the changed path according to a direction of the changed path; and a lens configured to receive the light having the changed optical path length from the optical path length control element, and to irradiate the received light onto the subject, wherein the optical path control unit comprises a mirror configured to rotate by a degree of rotation about a fixed axis of rotation each time the optical path control unit changes the path of the light, wherein a cross-section of the optical path control element has a wedge shape.

2. The optical probe of claim 1, wherein the optical path length control element is further configured to transmit the light having the changed path through the optical path length control element, and change the optical path length of the light according to a point of the optical path length control element through which the light passes.

3. The optical probe of claim 2, wherein the optical path length control element has a nonuniform thickness, and comprises a material having a uniform refractive index.

4. The optical probe of claim 3, wherein at least one surface of the optical path length control element has a meniscus shape.

5. The optical probe of claim 2, wherein the optical path length control element comprises at least two materials having different refractive indexes.

6. The optical probe of claim 2, wherein the optical path length control element comprises protrusions on a surface of the optical path length control element.

7. An optical coherence tomography (OCT) apparatus for scanning a subject by irradiating light onto the subject, the apparatus comprising:
a light source configured to generate light;
a light coupler configured to split the generated light into a measurement light and a reference light, transmit the measurement light to an optical probe, and receive a response light from the optical probe, the response light being produced by the measurement light reflecting from the subject;
a sensor configured to detect an interference signal generated by interference between the response signal and the reference signal; and
an image signal processor configured to generate a tomographic image of the subject from the detected interference signal;
wherein the light coupler comprises a beam splitter and a reference mirror,
wherein the optical probe comprises
an optical path control unit configured to receive the measurement light from the light coupler, and to change a path of the measurement light within the optical probe by repeatedly moving a direction in which the measurement light is irradiated onto the subject by a constant lateral distance,
an optical path length control element configured to receive the measurement light having the changed path from the optical path control unit, and to increase an optical path length of the measurement light having the changed path by a constant value each time the direction in which the measurement light is irradiated onto the subject moves by the constant lateral distance by changing a diameter of the measurement light having the changed path by blocking a portion of the measurement light having the changed path according to a direction of the changed path, and a lens configured to receive the measurement light having the changed optical path length from the optical path length control element, and to irradiate the measurement light output from the optical output unit onto the subject, wherein the optical path control unit comprises a mirror configured to rotate by a degree of rotation about a fixed axis of rotation each time the optical path control unit chances the path of the light, wherein a cross-section of the optical path control element has a wedge shape.

8. The apparatus of claim 7, wherein the optical path length control element is further configured to transmit the measurement light having the changed path through the optical path length control element, and change the optical path length of the measurement light according to a point of the optical path length control element through which the measurement light passes.

9. The apparatus of claim 8, wherein the optical path length control element has a nonuniform thickness, and comprises a material having a uniform refractive index.

10. The apparatus of claim 9, wherein at least one surface of the optical path length control element has a meniscus shape.

11. The apparatus of claim 8, wherein the optical path length control element comprises at least two materials having different refractive indexes.

12. The apparatus of claim 8, wherein the optical path length control element comprises protrusions on a surface of the optical path length control element.

13. An optical probe comprising:
an optical path control unit configured to receive light, and to change a path of the light by repeatedly moving a direction in which the light is irradiated onto a subject by a constant lateral distance; and
a scan lens having no moving parts and being configured to receive the light having the controlled path from the optical path control unit, and to modulate an optical path length of the light having the controlled path by increasing the optical path length of the light having the controlled path by a constant value each time the direction in which the light is irradiated onto the subject moves by the constant lateral distance by changing a diameter of the light having the controlled path by blocking a portion of the light having the controlled path according to a direction of the controlled path,
wherein the optical path control unit comprises a mirror configured to rotate by a degree of rotation about a fixed axis of rotation each time the optical path control unit changes the path of the light.

14. The optical probe of claim 13, wherein the scan lens is a passive optical path length modulator configured to modulate the optical path length of the light having the controlled path without any external control as the optical path control unit controls the path of the light.

15. The optical probe of claim 13, wherein the scan lens is further configured to modulate the optical path length of the light having the controlled path according to a characteristic of the optical path length modulator depending on a point where the light having the controlled path is incident on the optical path length modulator.

16. The optical probe of claim 15, wherein the characteristic of the scan lens is an optical path length of the scan lens.

* * * * *